United States Patent [19]
Kubota et al.

[11] Patent Number: 4,961,424
[45] Date of Patent: Oct. 9, 1990

[54] ULTRASONIC TREATMENT DEVICE

[75] Inventors: Tatsuya Kubota, Tokyo; Masakazu Gotanda, Sagamihara; Shinji Hatta, Tokyo; Hitoshi Karasawa, Tokyo; Tetsumaru Kubota, Tokyo; Takeaki Nakamura, Tokyo; Syuichi Takayama, Tokyo; Hiroshi Sasaki, Tokyo, all of Japan

[73] Assignee: Olympus Optical Co., Ltd., Tokyo, Japan

[21] Appl. No.: 225,030

[22] Filed: Jul. 27, 1988

[30] Foreign Application Priority Data

Aug. 5, 1987 [JP] Japan .................... 62-194298
Aug. 5, 1987 [JP] Japan .................... 62-194303
Aug. 7, 1987 [JP] Japan .................... 62-197806
Aug. 13, 1987 [JP] Japan .................... 62-200941
Aug. 13, 1987 [JP] Japan .................... 62-200942

[51] Int. Cl.⁵ .......................................... G01N 29/00
[52] U.S. Cl. .................................................. 128/24 A

[58] Field of Search ................. 128/24 A, 305; 604/22

[56] References Cited

U.S. PATENT DOCUMENTS 4,330,278  5/1982  Martin ................... 128/24 A X
4,504,264  3/1985  Kelman .................. 604/22
4,526,571  7/1985  Wuchinich ............. 128/24 A X Primary Examiner—Francis Jaworski
Attorney, Agent, or Firm—Frishauf, Holtz, Goodman & Woodward

[57] ABSTRACT

A therapeutical device using ultrasonic vibration includes an ultrasonic vibration generator for generating ultrasonic vibration in the axial direction of the device and in a direction different from the axial direction of the device, an amplifier connected to the ultrasonic vibration generator for amplifying the ultrasonic vibration generated, and a vibration transmitting connected to the amplifier member for transmitting the ultrasonic vibration.

2 Claims, 12 Drawing Sheets

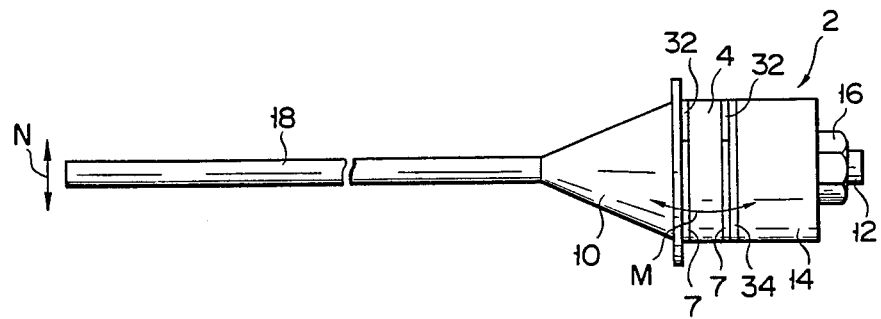
F I G. 21
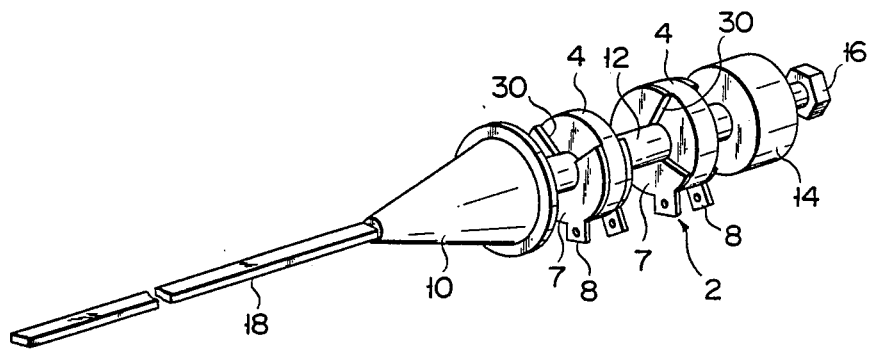
F I G. 22
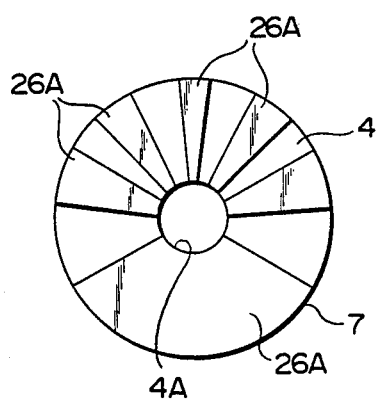
F I G. 23
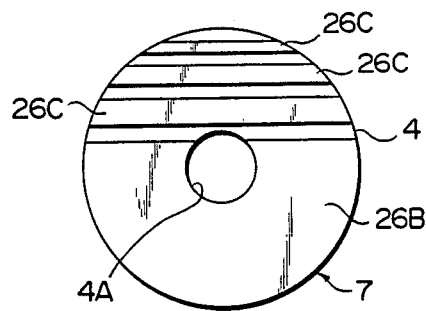
F I G. 24

4,961,424

ULTRASONIC TREATMENT DEVICE

BACKGROUND OF THE INVENTION

1. Field of the Invention

The present invention relates to a therapeutical device which uses supersonic i.e. ultrasonic vibration to destroy and emulsify concretionary or tissue in the cavity of a human body.

2. Description of the Related Art

The typical supersonic therapeutical device includes a supersonic vibrator and a member for transmitting supersonic vibration generated by this supersonic vibrator. The foremost end of the vibration transmitting member is pressed against concretionary or tissue in the cavity of the human body to destroy and emulsify it.

The supersonic vibrator used is of an electrostriction type and a magneto-striction type and in the case of this supersonic vibrator of the electrostriction type, for example a piezoelectric transducer having a bolted construction of the Langevin type, plural piezoelectric elements and electrodes are alternately placed one upon the other. Supersonic vibration generated by impressing voltage to the electrodes is amplified by a horn and transmitted to the vibration transmitting member.

The above-described typical supersonic therapeutical device is made symmetrical in relation to a point, taking its axial line as its center. Therefore, the supersonic vibration generated by impressing voltage to the electrodes becomes uniform on a plane perpendicular to the center axis and as the result, the direction in which the vibration is directed is limited only to the one along the axial line.

When the vibration transmitting member which vibrates only along the axial line is contacted with the matter to be treated, the matter to be treated is shocked only in one direction, so that the process of destroying and emulsifying the matter cannot be carried out with high efficiency.

SUMMARY OF THE INVENTION

The object of the present invention is to provide a supersonic therapeutical device capable of destroying and emulsifying concretionary or tissue in the cavity of human body with a higher efficiency by means of the vibration transmitting member.

This object of the present invention can be achieved by a supersonic therapeutical device comprising a supersonic vibration generator for generating supersonic vibration in a direction along its axial line and in another direction different from the axial direction, an amplifier member connected to the supersonic vibration generator to amplify the supersonic vibration thus generated, and a vibration transmitting member connected to the amplifier member to transmit the supersonic vibration.

This supersonic therapeutical device according to present invention includes the supersonic vibration generator means for generating supersonic vibration in the axial direction and in a direction different from the axial direction. Therefore, the vibration transmitting member can be vibrated both in the axial direction and in a direction perpendicular to the axial direction, so that the treatment of destroying and emulsifying concretionary or tissue, for example, in the cavity of the human body can be achieved with higher efficiency and reliability.

BRIEF DESCRIPTION OF THE DRAWINGS

FIGS. 20 and 21 are perspective and side views showing a variation of the electrode.

FIG. 22 is a perspective view showing variations of the electrode and the piezoelectric element.

FIGS. 23 and 24 are front views showing other variations of the electrodes.

DETAILED DESCRIPTION OF THE PREFERRED EMBODIMENTS

Figure 1:
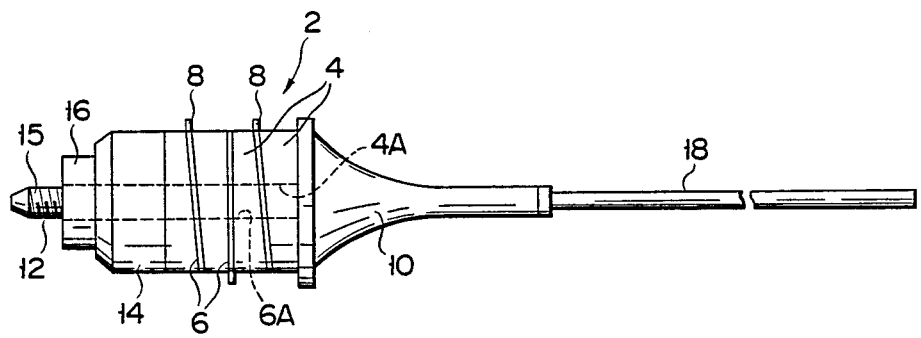
FIG. 1 is a side view showing a first embodiment of the supersonic therapeutical device according to the present invention.
Figure 2:
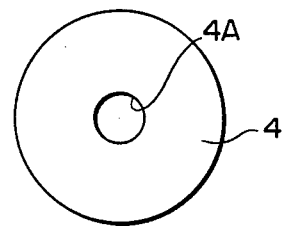
FIGS. 2 and 3 are front and sectional views showing a piezoelectric element employed by the supersonic therapeutical device in FIG. 1.
Figure 3:
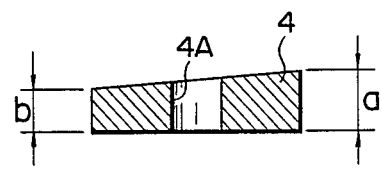

FIGS. 1 through 3 show a first embodiment of the supersonic therapeutical device according to the present invention. The supersonic therapeutical device shown in FIG. 1 has supersonic vibrator 2 located therein. This supersonic vibrator 2 includes plural disk-shaped piezoelectric elements 4 and electrodes 6 for generating the supersonic vibration, horn 10 for amplifying the vibration, and member 18 for transmitting the vibration. Plural piezoelectric elements 4 and electrodes 6 are alternately placed one upon the other. As shown in FIGS. 2 and 3, piezoelectric element 4 has through-hole 4A in the center thereof and when sectioned, it has a substantially wedge-like shape. Since the thickness of piezoelectric element 4 denoted by (a) at an end thereof is viewed in the radial direction thereof, it therefore appears to be larger than (b) of piezoelectric element 4 at the opposite end thereof. Namely, piezoelectric element 4 has a non-uniform thickness, which becomes thinner as it extends from one end to the opposite end in the radial direction thereof.

Through-hole 6A is formed in the center of electrode 6, similarly to piezoelectric element 4, and terminal 8 to which a lead line (not shown) is connected is projected from the outer circumference of electrode 6. Further, attaching rod 12 projects outward from the back end face of horn 10 and has male thread 15 positioned on the back portion thereof. Attaching rod 12 is inserted through through-holes 4A and 6A of piezoelectric elements 4 and electrodes 6, and holder member 14 is attached to rod 12 so as to, contact last piezoelectric element 4. Further, nut 16 is screwed onto the portion projecting from the back end face of holder member 14. Plural laminated piezoelectric elements 4 and electrodes 6 are clamped and held between horn 10 and holder member 14.

Elongated vibration transmitting member 18 is fixed to the foremost end of horn 10. Terminals 8 of electrodes 6 in supersonic vibrator 2 are connected to a power source through lead lines (not shown).

When a voltage is applied to piezoelectric elements 4 through electrodes 6 of supersonic vibrator 2, an electrorestrictive strain phenomenon occurs in the piezoelectric elements 4, and the supersonic vibration caused therefrom is amplified by horn 10 and transmitted to vibration transmitting member 18. By passing through a channel of an endoscope, vibration transmitting member 18 is introduced into the cavity of human body so that its foremost end is pressed against concretionary or tissue to destroy and emulsify the concretionary or tissue.

Each of piezoelectric elements 4 in supersonic vibrator 2 employed by the first embodiment of the present invention has a non-uniform thickness, or has a wedge-like shape. Therefore, the electrorestrictive strain is not uniformly applied to the plane of each of piezoelectric elements 4 when voltage is applied to piezoelectric elements 4 through electrodes 6. The supersonic vibration generated by supersonic vibrator 2 not only vibrates in the axial direction of the concretionary or tissue, but it also vibrates in a direction slanted relative to the axial direction thereof. The foremost end of vibration transmitting member 18 is thus vibrated in the direction perpendicular to the axial direction as well as in the axial direction of the concretionary or tissue. This enables vibration transmitting member 18 to apply the supersonic vibration to the concretionary or tissue in its axial and traverse directions, so that the concretionary or tissue can be destroyed and emulsified with a higher efficiency and reliability.

Figure 4:
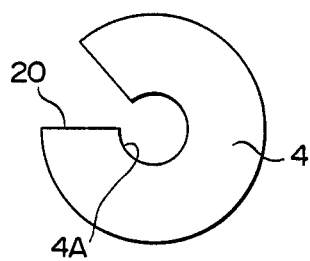
FIGS. 4 through 6 are front views showing variations of the piezoelectric element.
Figure 5:
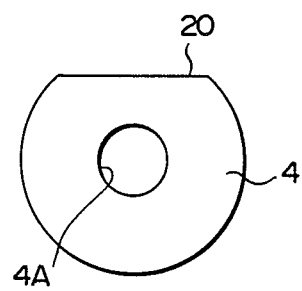
Figure 6:
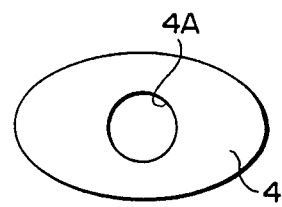

Although piezoelectric elements 4 employed by the first embodiment of the present invention have a wedge-like shape when sectioned, the same effect can be achieved when the piezoelectric elements 4 have cut-away portion 20, as shown in FIGS. 4 and 5, or have an elliptical-shape, as shown in FIG. 6. In short, each of piezoelectric elements 4 may have a non-uniform thickness to cause the vibration generated therefrom to be directed in a plurality of directions.

Figure 7:
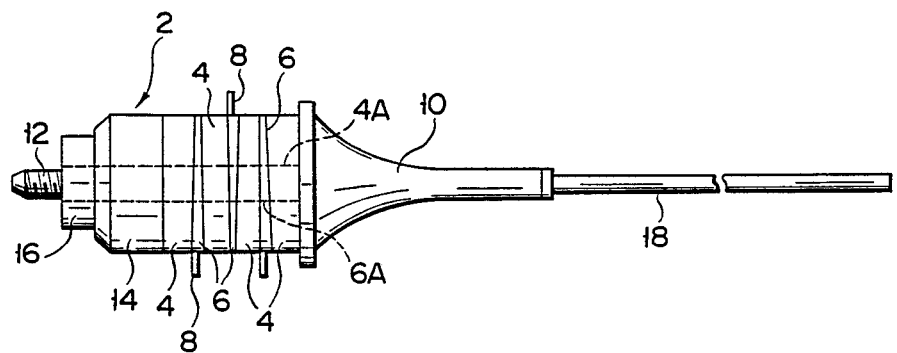
FIG. 7 is a side view showing a variation of the first supersonic therapeutical device.
Figure 8:
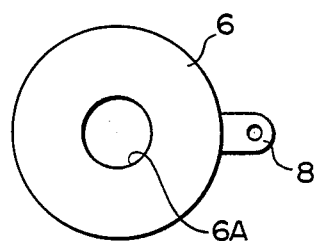
FIGS. 8 and 9 are front and sectional views showing an electrode employed by the supersonic therapeutical device in FIG. 7.

A modification of the first supersonic vibrator will be described with reference to FIGS. 7 through 9.

Figure 9:
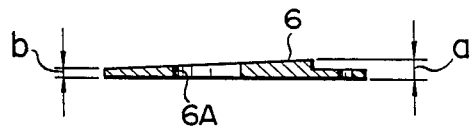

Also in this varied supersonic vibrator 2, electrode 6 is formed to have a non-uniform thickness, or has a wedge-like shape, as shown in FIG. 9. Initial bias added to piezoelectric elements 4 through electrodes 6 becomes irregular in accordance with the non-uniformity of electrode 6. The supersonic vibration generated by supersonic vibrator 2 is thus caused not only in the axial direction but also in the direction slanted relative to the axial direction, thereby enabling the foremost end of vibration transmitting member 18 to be vibrated in the axial direction and also in the traverse direction perpendicular to the axial direction. As the result, vibration transmitting member 18 applies the supersonic vibration to concretionary or tissue in the axial and traverse directions, so that destruction and emulsification of concretionary or tissue can be achieved with higher efficiency and reliability.

The merit of vibrating the foremost end of the vibration transmitting member in the traverse direction can also be gained when a recess or through-hole is formed in electrode 6 to make this electrode 6 irregular in thickness.

A second embodiment of the supersonic therapeutical device according to the present invention will be described with reference to FIGS. 10 through 14.

Figure 10:
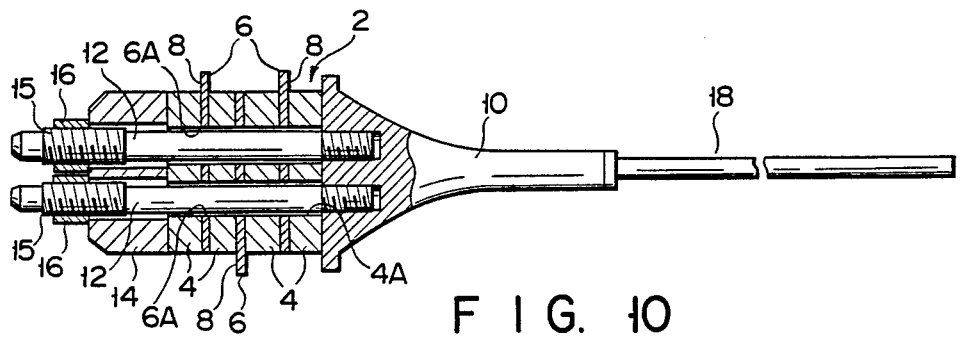
FIG. 10 is a side view showing a second embodiment of the supersonic therapeutical device partly cut away.
Figure 11:
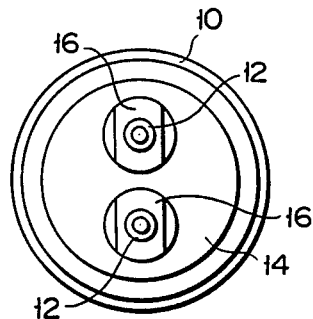
FIG. 11 is a back view showing the supersonic therapeutical device in FIG. 10.
Figure 12:
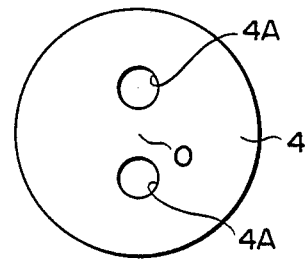
FIG. 12 is a front view showing a piezoelectric element employed by the supersonic therapeutical device in FIG. 10.

The supersonic therapeutical device shown in FIG. 10 has supersonic vibrator 2. This supersonic vibrator 2 includes plural disk-like piezoelectric elements 4 and electrodes 6, which are alternately placed one upon the other. A pair of through-holes 4A are formed in each of piezoelectric elements 4 and they are shifted from the center of piezoelectric element 4, as shown in FIGS. 10 through 12. Namely, they are shifted outward from center (0) of piezoelectric element 4 in the radial direction by the same distance.

A pair of through-holes 6A are also formed in each of electrodes 6 and they are shifted from the center of electrode 6, similarly to those of piezoelectric element 4. Through-holes 4A and 6A of piezoelectric elements 4 and electrodes 6 are fitted onto a pair of attaching rods 12 projected from the back end face of horn 10. Holder member 14 is attached to attaching rods 12, contacting with last piezoelectric element 4, and nuts 16 are screwed onto male threads 15 formed on those portions of attaching rods 12 which are projected from the back end face of holder member 14. Plural laminated piezoelectric elements 4 and electrodes 6 are therefore clamped and fixed by horn 10 and holder member 14.

Vibration transmitting member 18 is attached to the foremost end of horn 10 and terminals 8 of electrodes 6 in supersonic vibrator 2 are connected to a power source through lead lines (not shown).

According to the second embodiment of the supersonic therapeutical device, supersonic vibration is generated due to electrorestrictive strain phenomenon of piezoelectric elements 4 when voltage is applied to piezoelectric elements 4 through electrodes 6 in supersonic vibrator 2, and this supersonic vibration is amplified by horn 10 and transmitted to vibration transmitting member 18.

Electrodes 6 of supersonic vibrator 2 are clamped at their positions shifted from their center by means of nuts 16. When the clamping forces of nuts 16 are changed to add different clamping forces to piezoelectric elements 4, therefore, initial bias added to piezoelectric elements 4 can be made irregular. As the result, the supersonic vibration generated by supersonic vibrator 2 becomes irregular, vibrating not only in the axial direction but also in the direction slanted relative to the axial direction, so that the foremost end of vibration transmitting member 18 can also be vibrated in the traverse direction perpendicular to the axial direction. Therefore, vibration transmitting member 18 can add the supersonic vibration to concretionary or tissue in the axial and traverse directions, thereby enabling the concretionary or tissue to be destroyed and emulsified with higher efficiency and reliability.

Figure 13:
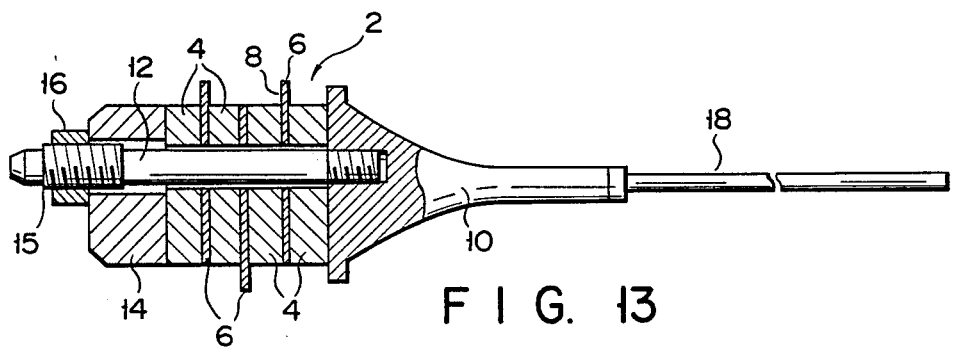
FIG. 13 is a side view showing a variation of the second supersonic therapeutical device partly cut away.
Figure 14:
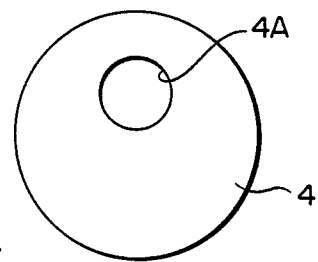
FIG. 14 is a front view showing a piezoelectric element employed by the supersonic therapeutical device in FIG. 13.

According to the second embodiment, a pair of attaching rods 12 are attached to but shifted from the center of the back end face of horn 10, and a pair of nuts 16 are screwed onto male threads 15 of these attaching rods 12 with different forces, so that different clamping forces can be added to piezoelectric elements 4. As shown in FIG. 13, however, one attaching rod 12 may be attached to but shifted from the center of the back end face of horn 10, and one nut 16 may be screwed onto male thread 15 of attaching rod 12 so as to clamp piezoelectric elements 4 with irregular clamping force. As shown in FIG. 14 it may be arranged in this case that through-hole 4A is formed in each of disk-like piezoelectric elements 4, shifting from the center thereof, and that through-hole 6A is also formed in each of disk-like electrodes 6 (not shown), shifting from the center thereof.

Figure 15:
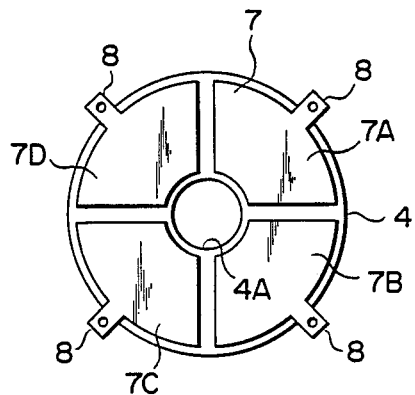
FIG. 15 is a front view showing an electrode employed by a third embodiment of the supersonic therapeutical device according to the present invention.

A third embodiment of the supersonic therapeutical device according to the present invention will be described referring to FIGS. 15 through 17.

Figure 16:
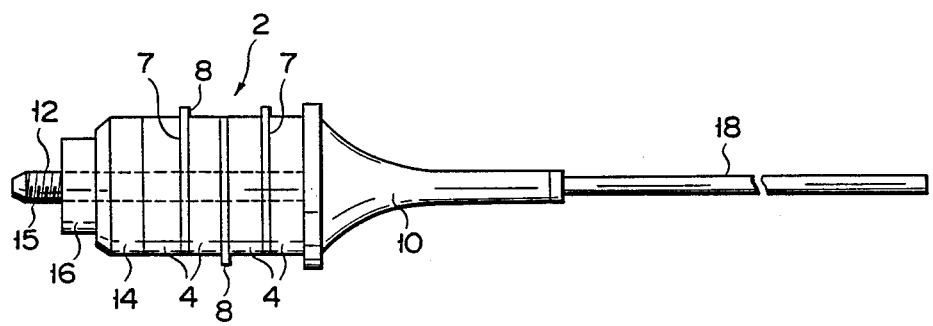
FIG. 16 is a side view showing the third embodiment of the supersonic therapeutical device according to the present invention.
Figure 17:
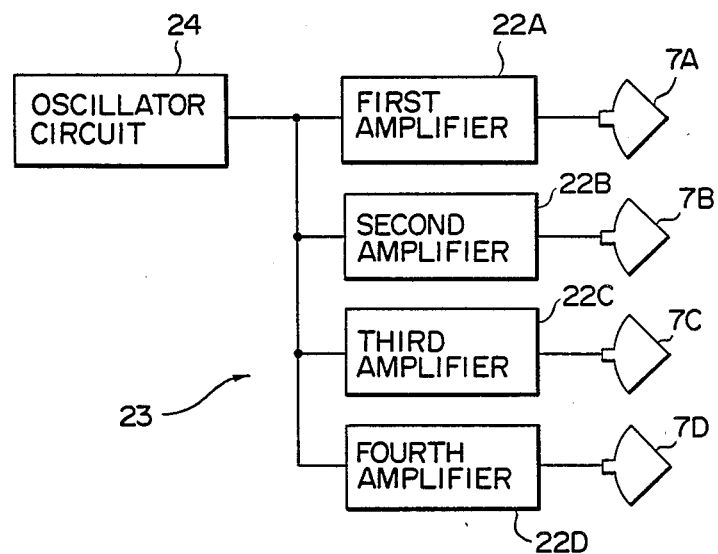
FIG. 17 is a block diagram showing a voltage supply means employed by the third embodiment of the supersonic therapeutical device according to the present invention.

This third supersonic therapeutical device has supersonic vibrator 2, as shown in FIG. 16. Supersonic vibrator 2 includes plural piezoelectric elements 4 and electrodes 7, which are alternately placed one upon the other. Each of piezoelectric elements 4 is shaped in a disk, having through-hole 4A in the center thereof, as shown in FIG. 15. Each of electrodes 7 is divided into first to fourth electrode pieces 7A-7D, which are contacted with end faces of piezoelectric elements 4, and each of electrode pieces 7A-7D is shaped like a fan, having a vertical angle of about 90°. Through-holes 4A of piezoelectric elements 4 are fitted onto attaching rod 12 which is projected from the back end face of horn 10. Further, holder member 14 is contacted with last piezoelectric element 4 and nut 16 is screwed onto male thread 15 formed on that portion of attaching rod 12 which is projected from the back end face of holder member 14. Plural laminated piezoelectric elements 4 and electrodes 7 are therefore clamped and fixed by horn 10 and holder member 14. Pipe-like vibration transmitting member 18 is connected to the foremost end of horn 10 and serves to transmit supersonic vibration amplified by horn 10.

Voltage supply device 23 has four amplifiers 22A-22D and oscillator circuit 24. First to fourth amplifiers 22A-22D which can freely adjust their outputs are connected to first to fourth electrode pieces 7A-7D of each of electrodes 7 through terminals 8. These amplifiers 22A-22D are connected to oscillator circuit 24. Therefore, voltage of some optional value can be applied to electrode pieces 7A-7D of each of electrodes 7 through oscillator circuit 24 and amplifiers 22A-22D.

When voltage is applied to piezoelectric elements 4 through electrode pieces 7A-7D of each of electrodes 7 in supersonic vibrator 2 in the case of third supersonic therapeutical device, supersonic vibration is generated due to the electrorestrictive strain phenomenon of each of piezoelectric elements 4, amplified by horn 10 and transmitted to vibration transmitting member 18. When vibration transmitting member 18 is introduced into the of human a body, passing through a channel of the endoscope, for example, and its foremost end is pressed against concretionary or tissue, therefore, the concretionary or tissue can be destroyed and emulsified.

Each of electrodes 7 in supersonic vibrator 2 is divided into plural electrode pieces 7A-7D, which are attached to end faces of piezoelectric elements 4. When outputs of first to fourth amplifiers 22A-22D are adjusted to apply different voltages to respective electrode pieces 7A-7D, therefore, supersonic vibration generated by piezoelectric elements is directed not only in the axial direction but also in a direction slanted relative to the axial direction. The foremost end of vibration transmitting member 18 is thus vibrated in a direction perpendicular to the axial direction as well as in the axial direction. The treatment of destroying and emulsifying concretionary or tissue which could not be done with high efficiency when the foremost end of vibration transmitting member 18 was vibrated only in one axial direction can be therefore carried out with higher efficiency and reliability. In addition, when outputs of first to fourth amplifiers 22A-22D are adjusted to change values of those voltages which are applied to respective piezoelectric elements 4, direction and magnitude of vibration to which vibration transmitting member is subjected can be changed.

Figure 18:
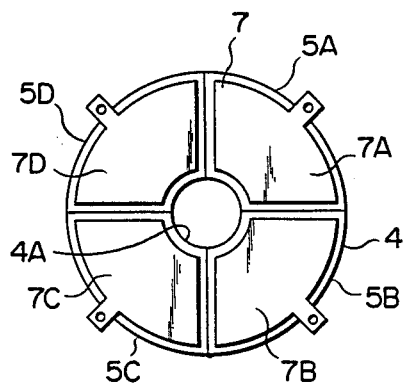
FIG. 18 is a front view showing a variation of the piezoelectric element employed by the third supersonic therapeutical device.

FIG. 18 shows a modification of the third embodiment according to the present invention. Each of piezoelectric elements 4 is divided into four element pieces 5A-5D in this case, as electrode 7 is divided, and each of element pieces is shaped like a fan, having a vertical angle of about 90°. When this variation is arranged as described above, vibration transmitting member 18 can also be vibrated in the traverse direction.

Figure 19:
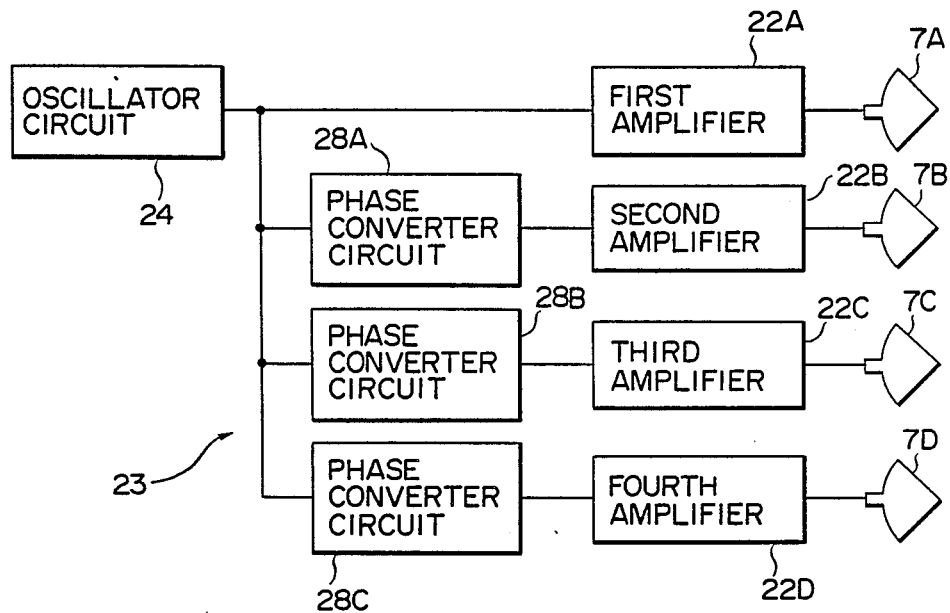
FIG. 19 is a block diagram showing a variation of the voltage supply device.

FIG. 19 shows a second modification of the third embodiment according to the present invention. Second to fourth amplifiers 22B-22D of voltage supply device 23 are connected to oscillator circuit 24 through their respective phase converter circuits 28A-28C in this case. Therefore, values of those voltages which are applied to electrode pieces 7A-7D of electrodes 7 can be changed together with phases of these high frequency voltages, thereby enabling vibration generated by piezoelectric elements 4 to be made more irregular.

Figure 20:
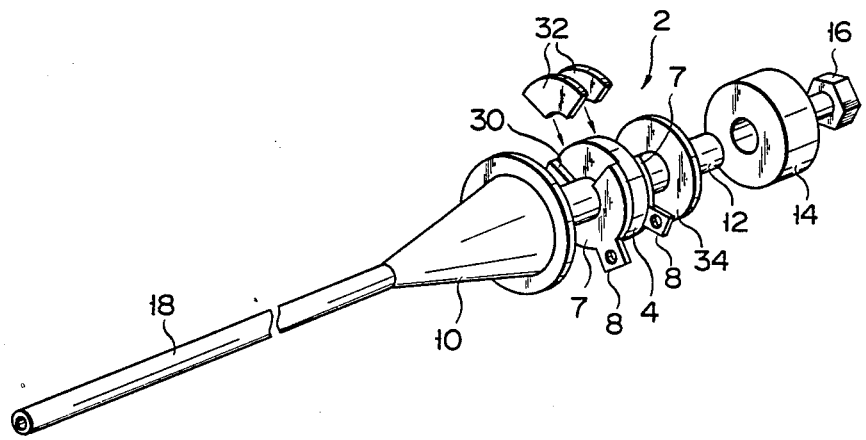

FIGS. 20 and 21 show a third modification. A part of each of disk-like electrodes 7 which are contacted with both end faces of one piezoelectric element 4 is cut away to form a fan-like cut-away portion 30 and spacer 32 is inserted into this cut-away portion 30. Further, insulation plate 34 is arranged between holder member 14 and rear electrode 7.

Voltage applied to piezoelectric element 4 is made not constant because electrodes 7 have cut-away portions 30, and the vibration pattern of piezoelectric element 4 draws an arc not parallel to the axial line of supersonic vibrator 2, as shown by (M) in FIG. 21. Therefore, the foremost end of vibration transmitting member 18 is vibrated in the traverse direction, too, as shown by (N) in FIG. 21.

FIG. 22 shows a fourth modification. This fourth modification of supersonic vibrator 2 has two piezoelectric elements 4 with both end faces of which electrodes 7 each provided with cut-away portion 30 are contacted. Cut-away portions 30 of two electrodes 7 which are contacted with both end faces of one piezoelectric element 4 are shifted along the circumference of piezoelectric element 4 from those of two electrodes 7 which are contacted with both end faces of the other piezoelectric element 4. A probe having a rectangular section is used as vibration transmitting member 18. Directions in which the foremost end of vibration transmitting member 18 is vibrated can be changed by adjusting the extent by which cut-away portions 30 of two electrodes 7 which are contacted with both end faces of one piezoelectric element 4 are shifted from those of two electrodes 7 which are contacted with both end faces of the other piezoelectric element 4.

FIG. 23 shows a variation of electrode 7 wherein electrode 7 contacted with the end face of piezoelectric element 4 comprises a plurality of fan-like electrode pieces 26A which are different in size. FIG. 24 shows another variation of electrode 7 wherein electrode 7 comprises semi-circular electrode piece 26B and plural strap-like electrode pieces 26C. When the electrode is shaped as shown in FIGS. 23 and 24 to apply irregular voltages to the piezoelectric elements, the same merits as those achieved by the third and fourth variations of supersonic vibrator 2 can be obtained.

A fourth embodiment of the supersonic therapeutical device according to the present invention will be described with reference to FIGS. 25 and 26.

Figure 25:
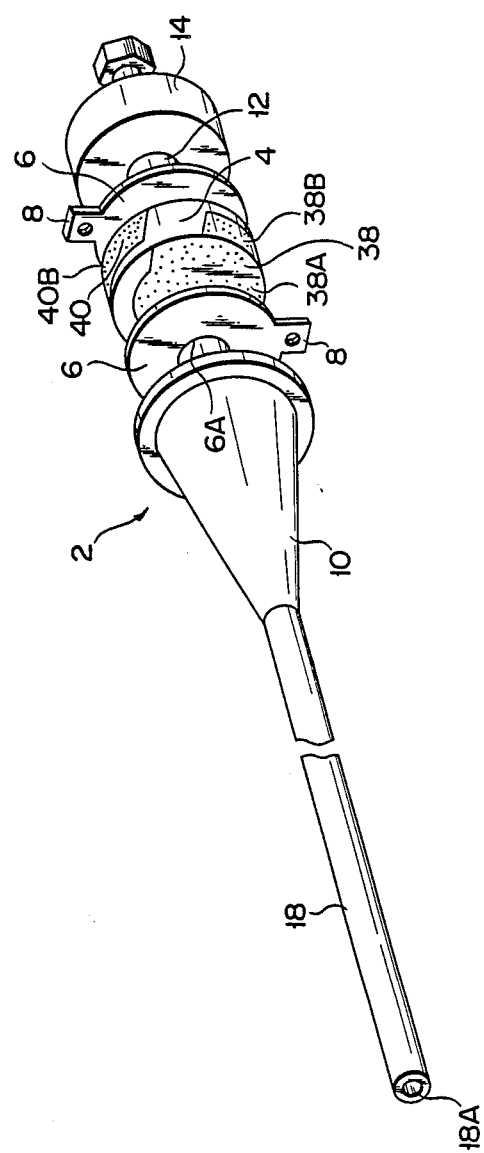
FIG. 25 is a perspective view showing a fourth embodiment of the supersonic therapeutical device according to the present invention.
Figure 26:
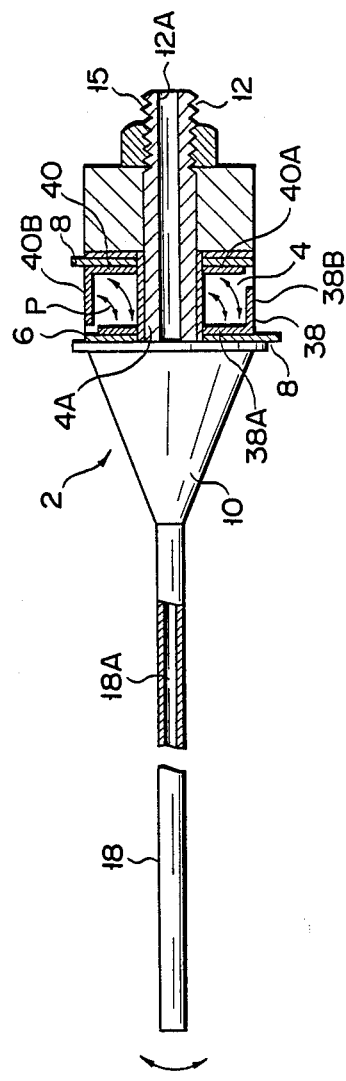
FIG. 26 is a side view showing the supersonic therapeutical device in FIG. 25 partly cut away.

The supersonic therapeutical device shown in FIGS. 25 and 26 has supersonic vibrator 2, which includes disk-like piezoelectric element 4 provided with through-hole 4A in the center thereof. First and second metal films 38 and 40 are vapor-deposited on piezoelectric element 4. First metal film 38 includes first end face portion 38A covering one end face of piezoelectric element 4 and first outer circumferential portion 38B covering a part of the outer circumferential face thereof, while second metal film 40 includes second end face portion 40A covering the other end face of piezoelectric element 4 and second outer circumferential portion 40B covering a part of the remaining outer circumferential face thereof.

Electrode plates 6 are contacted with metal films 38 and 40 on both end faces of piezoelectric element 4 and each of electrode plates 6 is provided with through-hole 6A in the center thereof and terminal 8 projected from the outer circumference thereof. The assembly of piezoelectric element 4 and a pair of electrode plates 6 is connected integral to horn 10 in such a way that through-holes 4A and 6A of piezoelectric element 4 and electrode plates 6 are fitted onto attaching rod 12 which is projected from the back end face of horn 10 and that nut 16 is screwed onto male thread 15 of attaching rod 12 through holder member 14.

Vibration transmitting member 18 is connected to the foremost end of horn 10. Vibration transmitting member 18 is a pipe having through-hole 18A therein and this through-hole 18A is communicated with through-hole 12A which is passed through attaching rod 12 in the axial direction thereof. Through-hole 12A in attaching rod 12 is also communicated with a vacuum pump (not shown).

Voltage is applied to piezoelectric element 4 through a pair of electrode plates 6 and first and second metal films 38 and 40. As the result, supersonic vibration is generated due to electrorestrictive strain phenomenon of this piezoelectric element 4, amplified by horn 10 and then transmitted to vibration transmitting member 18.

First and second metal films 38 and 40 which are vapor-deposited on piezoelectric element 4 of supersonic vibrator 2 cover the outer circumferential face of piezoelectric element 4 as well as the end faces thereof. Therefore, voltage is applied to piezoelectric element 4 in the axial direction perpendicular to the end face of piezoelectric element 4 and also between end face portions 38A, (40A) and outer circumferential portions, 40B, (38B) of metal films 38 and 40, as shown by arrows (P) in FIG. 26. More specifically, voltage is also applied to piezoelectric element 4 in a direction parallel to the end face of piezoelectric element 4. The foremost end of vibration transmitting member 18 is thus vibrated in the traverse direction as well as in the backward and forward direction. This enables the treatment of destroying and emulsifying concretionary or tissue, which could not be well done by vibration transmitting member 18 whose foremost end was vibrated only in forward and backward direction, to be carried out with higher efficiency and reliability.

Figure 27:
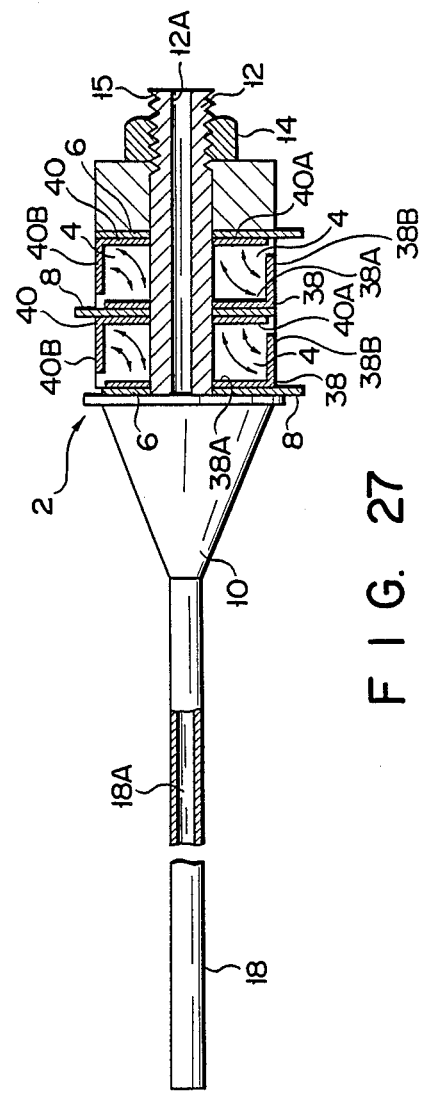
FIG. 27 is a side view showing a first variation of the fourth supersonic therapeutical device partly cut away.

FIG. 27 shows a first modification of a fourth supersonic therapeutical device wherein two piezoelectric elements 4 on each of which first and second metal films 38 and 40 are vapor-deposited as described above, are arranged side by side.

Figure 28:
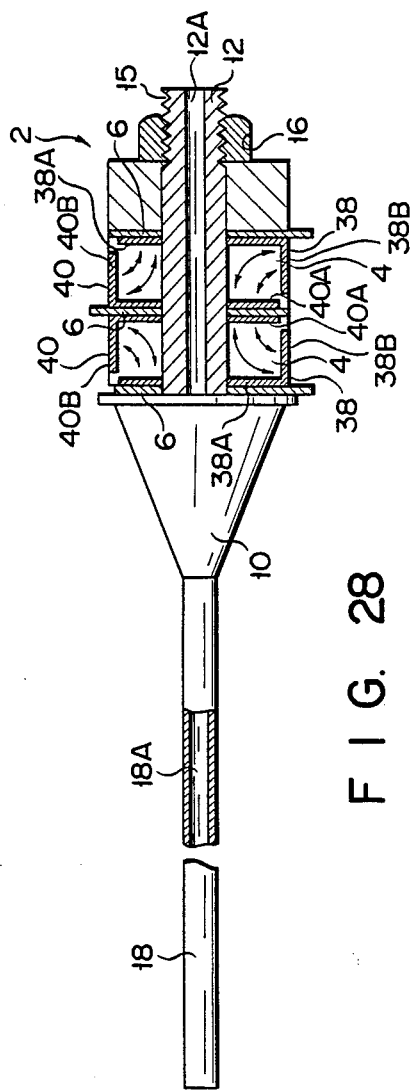
FIG. 28 is a side view showing a second variation of the fourth supersonic therapeutical device partly cut away.

FIG. 28 shows a second modification wherein two piezoelectric elements 4 are arranged side by side as seen in the first modification but metal films 38 and 40 are vapor-deposited on these piezoelectric elements 4 in such a way that the direction of voltage added to one piezoelectric element 4 is made reverse to that of a voltage added to the other piezoelectric element 4.

Figure 29:
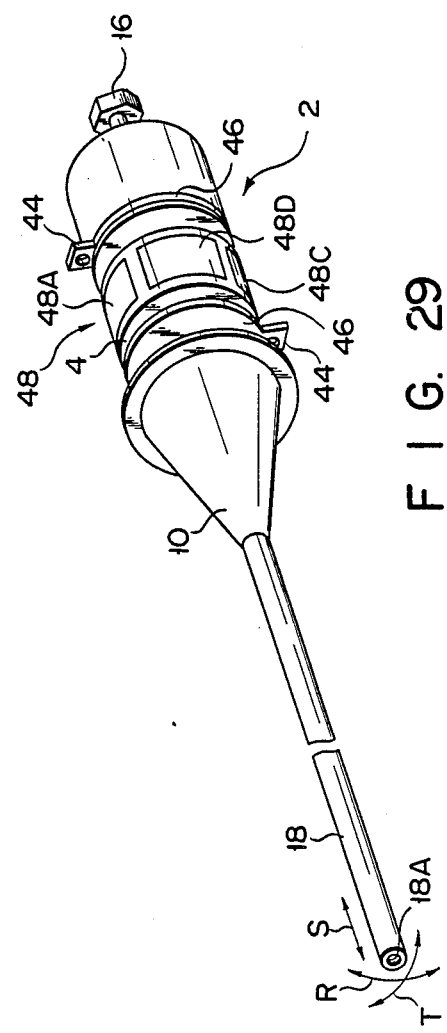
FIG. 29 is a perspective view showing a third variation of the fourth supersonic therapeutical device.
Figures 30, 31:
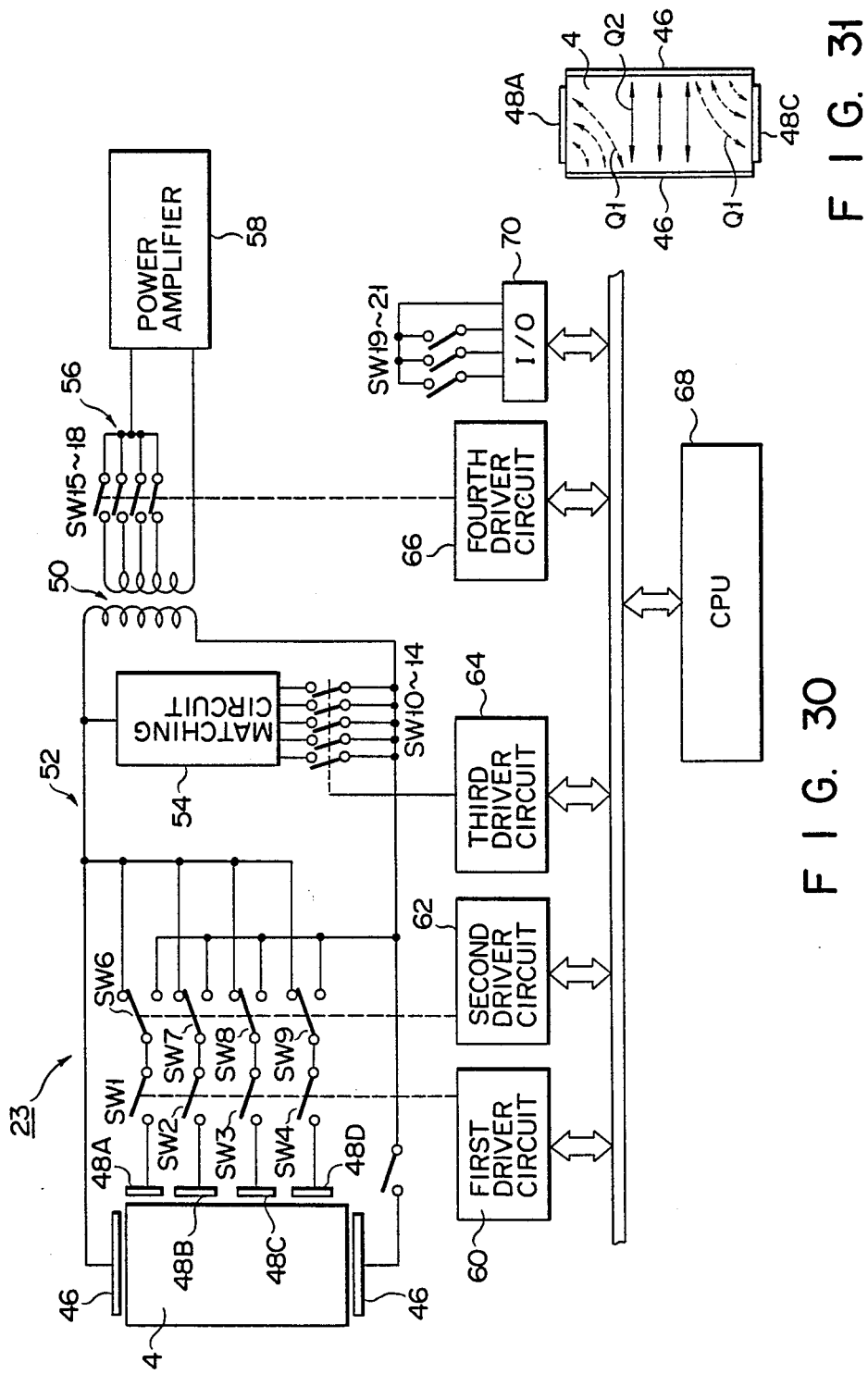
FIG. 30 is a block diagram showing a voltage supply device employed by the third variation of the supersonic therapeutical device.
FIG. 31 is a side view showing piezoelectric elements employed by the supersonic therapeutical device in FIG. 29.

FIGS. 29 through 31 show a third modification of the fourth supersonic therapeutical device. End face electrodes 46 are contacted with both end faces of piezoelectric element 4, respectively, and first to fourth peripheral electrodes 48A–48D of electrode 48 are arranged on the periphery of piezoelectric element 4 at an interval angle of 90° when viewed along the periphery of piezoelectric element 4. A pair of end face electrodes 46 are connected to secondary circuit 52 of coupling transformer 50 of voltage supply device 23. Electrode changeover switches SW1–SW4 are connected to four peripheral electrodes 48A–48D, respectively, and polarity converting switches SW6–SW9 are connected in series to switches SW1–SW4, respectively. Switch SW5 for controlling power applied to end face electrodes 46 is connected in series to secondary circuit 52 of coupling transformer 50. Matching circuit 54 is also connected to secondary circuit 52 of coupling transformer 50 through SW10–SW14.

Primary circuit 56 of coupling transformer 50 is connected to power amplifier 58 of voltage supply device 23 and switches SW15–SW18 for changing over the matching of impedance are connected in series to primary circuit 56 of coupling transformer 50.

Switches SW1-SW4 are connected to first driver circuit 60 and switches SW6-SW9 are connected to second driver circuit 62. Further, switches SW10 SW14 are connected to third driver circuit 64 and switches SW15-SW18 are connected to fourth driver circuit 66.

Driver circuits 60-66 are connected to CPU68 of voltage supply device 23, to which input/output port 70 is connected. Connected to input/output port 70 are switches SW19-SW21 for selecting vertical, horizontal and rotational vibration modes.

The foremost end of vibration transmitting member 18 can be vibrated under various modes in this third modification of the supersonic therapeutical device when each of the switches is controlled by CPU68. When voltage is applied to piezoelectric element 4 between one end face electrode 46 and first peripheral electrode 48A and between the other electrode 46 and third peripheral electrode 48C, for example, as shown by broken arrows (Q1) in FIG. 31, the foremost end of vibration transmitting member 18 can be vibrated in up and down direction shown by an arrow (R) in FIG. 29. When voltage is applied to piezoelectric element 4 between one end face electrode 46 and second peripheral electrode 48B and between the other end face electrode 46 and fourth peripheral electrode 48D, it can be vibrated in left and right direction shown by an arrow (T) in FIG. 29. When changeover is made at a certain interval between the up and down (or vertical) vibration and the left and right (or horizontal) vibration, it can be vibrated almost in the rotational direction. When voltage is applied to piezoelectric element 4 between paired end face electrodes 46, as shown by solid arrows (Q2), it can be vibrated in forward and backward direction shown by an arrow (S) in FIG. 29.

The vibrating direction of the foremost end of vibration transmitting member 18 can be freely controlled in the case of this third modification.

It may be arranged in this third modification that plural peripheral electrodes are arranged on the periphery of piezoelectric element 4 with no end face electrode attached on both end faces thereof.

What is claimed is:

1. An ultrasonic treatment device, comprising:
   an ultrasonic vibration generator;
   amplifier means, connected to said ultrasonic vibration generator, for amplifying ultrasonic vibrations generated by said ultrasonic vibration generator; and
   vibration transmitting means, having an elongated portion and connected to said amplifier means, for transmitting the ultrasonic vibrations;
   said ultrasonic vibration generator including means for generating ultrasonic vibrations in the longitudinal axial direction and in a substantially lateral direction of the elongated portion of said transmitting means comprised of (a) a piezoelectric element, (b) both end faces of said piezoelectric element having an electrode attached thereto, said electrode comprising a plurality of electrode pieces, and (c) voltage supply means for applying voltages of different levels, respectively, to the electrode pieces.

2. The ultrasonic treatment device according to claim 1, wherein said voltage supply means has phase converter means for applying high frequency voltages having phases of different angles to the electrode pieces of each of said electrodes.

* * * * *

UNITED STATES PATENT AND TRADEMARK OFFICE
CERTIFICATE OF CORRECTION

PATENT NO. : 4,961,424
DATED : October 9, 1990
INVENTOR(S) : KUBOTA et al

It is certified that error appears in the above-identified patent and that said Letters Patent is hereby corrected as shown below:

Title page, item [56] References Cited -

Insert under "U.S. Patent Documents" the following reference:

--4,705,980  11/1987  Mishiro....310/323--.

Signed and Sealed this

Sixth Day of July, 1993

Attest:

MICHAEL K. KIRK

Attesting Officer

Acting Commissioner of Patents and Trademarks